United States Patent [19]

Inoue

[11] Patent Number: 5,030,196
[45] Date of Patent: Jul. 9, 1991

[54] MAGNETIC TREATMENT DEVICE

[75] Inventor: Kiyoshi Inoue, Tokyo, Japan

[73] Assignee: Inoue-Japax Research Incorporated, Yokohamashi, Japan

[21] Appl. No.: 514,356

[22] Filed: Jul. 15, 1983

Related U.S. Application Data

[63] Continuation of Ser. No. 257,851, Apr. 27, 1981, abandoned.

[30] Foreign Application Priority Data

| Apr. 23, 1980 | [JP] | Japan | 55-52852 |
| May 13, 1980 | [JP] | Japan | 55-63717 |
| May 30, 1980 | [JP] | Japan | 55-71483 |
| Jul. 18, 1980 | [JP] | Japan | 55-97574 |
| Jul. 28, 1980 | [JP] | Japan | 55-105672 |

[51] Int. Cl.⁵ ............................................. A61N 2/04
[52] U.S. Cl. .................................... 600/14; 600/15
[58] Field of Search ........................... 128/1.3–1.5; 600/9, 13, 14, 15

[56] References Cited

U.S. PATENT DOCUMENTS

| 3,658,051 | 4/1972 | MacLean | 128/1.5 |
| 3,911,930 | 10/1975 | Hagfors et al. | 128/422 X |
| 4,105,017 | 8/1978 | Ryaby et al. | 128/1.5 |
| 4,112,923 | 9/1978 | Tomecek | 128/1.3 |
| 4,233,965 | 11/1980 | Fairbanks | 128/1.5 |
| 4,262,672 | 4/1981 | Kief | 128/329 A |

FOREIGN PATENT DOCUMENTS

| 2736345 | 2/1979 | Fed. Rep. of Germany | 128/1.5 |
| 2342502 | 9/1977 | France | 128/735 |
| 688192 | 9/1979 | U.S.S.R. | 128/1.3 |

Primary Examiner—Lee S. Cohen
Attorney, Agent, or Firm—Herbert Dubno; Ronald Lianides

[57] ABSTRACT

A magnetic medical treatment device and method wherein a coil received in a housing is energized with a periodic current of a predetermined frequency furnished from a power supply accommodated in the housing or disposed separately outside thereof to produce a corresponding, time-varying periodic magnetic field through the coil. A stylus formed of magnetically permeable material and electromagnetically associated with the coil means is positioned in engagement with a preselected surface zone of the body surface of an individual (patient) to selectively apply the magnetic flux to the surface zone.

2 Claims, 8 Drawing Sheets

MAGNETIC TREATMENT DEVICE

This application is a continuation of application Ser. No. 257,851 filed Apr. 27, 1981, now abandoned.

FIELD OF THE INVENTION

The present invention relates to a magnetic treatment device. More particularly, it relates to an improved device for magnetic stimulation of the body acupuncture.

BACKGROUND OF THE INVENTION

It has been widely recognized that magnetism is effective to stimulate portions of a human body.

OBJECTS OF THE INVENTION

It is an important object of the present invention to provide an improved magnetic treatment device which is relatively simple and inexpensive.

Another important object of the invention is to provide a compact magnetic treatment device which can be used adjustably.

SUMMARY OF THE INVENTION

The present invention is based upon a discovery that an enhanced effect of magnetism is attained when the magnetic field or flux applied to a body surface is of periodically varying intensity of fluctuates in intensity with some periodicity. Thus, it has been found that an enhanced effect is achievable by providing a stylus member formed of a magnetically permeable material and having coil means associated therewith, energizing the coil means with a periodic or periodically fluctuating electric current of a predetermined frequency to produce a correspondingly fluctuating magnetic flux through the stylus member and positioning the stylus member in the proximity of (i.e. in contact with or spaced apart from) a preselected body surface zone to cause the magnetic flux to penetrate into the latter.

The improved magnetic treatment device according to the present invention thus comprises a stylus member formed of a magnetically permeable material positionable in the proximity of (i.e. in contact with or spaced apart from) a body surface, coil means electromagnetically associated with the stylus member, power supply means for passing through said coil means a periodic or periodically varying electric current to produce a corresponding varying magnetic field passing through the stylus member, and positioning means operable to position the stylus member in the proximity of the body surface to cause the varying magnetic field to penetrate into the body surface.

Sometimes the stylus member may be eliminated and the coil means with or without a core member disposed therein may itself be positioned in proximity of a desired portion on the patient's body surface. The coil means is energized with a periodic or periodically fluctuating electric current of a predetermined frequency to produce a correspondingly fluctuating magnetic field and flux passing through the coil means. The coil means may advantageously be received in a housing having a sticking element, e.g. of vacuum-type, for attaching the housing to a body surface and positioning the coil means in the proximity of the desired point or zone thereon.

BRIEF DESCRIPTION OF DRAWING

These and other specific objects, features and advantages of the present invention will become more readily apparent from the following description of certain preferred embodiments thereof, made with reference to the accompanying drawing in which.

SPECIFIC DESCRIPTION

Figure 1:
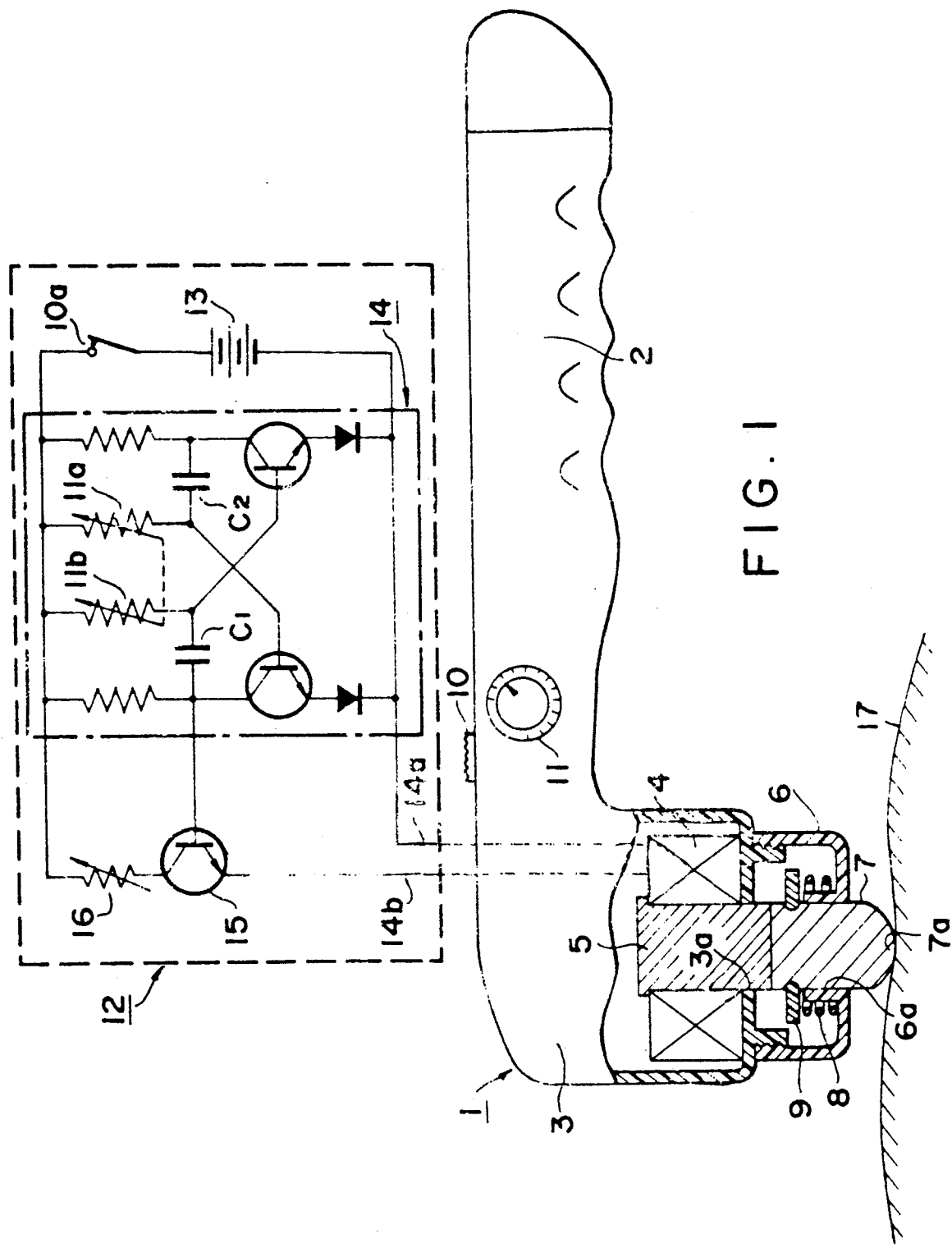
FIG. 1 is a schematic view diagrammatically illustrating a basic embodiment of the present invention.

In FIG. 1, a magnetic treatment device 1 is shown which comprises a handle 2 formed of nonmagnetic material terminating at a housing 3 in which an electromagnetic coil 4 is seated to surround a magnetically permeable core member 5. The core member 5 extends through an opening 3a formed through the floor of the housing 3 onto which a cup member 6 is threadedly fitted. A stylus member 7 formed of a magnetically permeable material arranged in contact with the core member 5 in the cup 6 projects from the latter by extending through an opening 6a thereof formed coaxially with the opening 3a of the housing 3. A helical spring 8 is seated in the cup 6 to surround the stylus member 7 and to act against a leaf spring 9 secured to the stylus member 7 thereby holding the latter in firm contact with the core member 5. The core member 5 may be secured to the coil 4 which is affixed in turn to the housing 3 or alternatively may be slidably passed through the coil 4 and resiliently held by a support member (not shown) secured to the housing 3.

The handle 10 is provided with a thumb switch 10, say, of slide type and a frequency-setting knob 11 of a rotary type. A power supply 12 for energizing the coil 4 is accommodated in the housing 3 (or the handle 2) and comprises a DC source 13, say, a battery, an oscillator 14 and a switching transistor 15. The DC source 13 and the power switch 15 form a series circuit connected to the coil 4 via a pair of output terminals 14a and 14b and including contacts 10a for the switch 10 and a variable resistor 16. The oscillator 14 is constituted by an astable multivibrator including a pair of variable resistors 11a and 11b ganged together and adjustable by means of the knob 11 to set, in conjunction with capacitors $C_1$ and $C_2$ (which may be of equal capacitance), the output frequency of the oscillator 15 in a predetermined range. Input signal pulses of the oscillator 14 are thus applied to the base of the switching transistor 15 to periodically connect the output of the DC source 13 at a preset frequency to the coil 4 via the terminals 14a and 14b. The power supply 12, though mentioned as accommodated in the housing 3, may alternatively be packaged in a separate unit outside the device 1. The DC source 13 may then be energized from a commercial AC source and comprise a transformer energizable by the AC source and a rectifier for converting the transformed AC output to a direct current.

With the coil 4 energized with the power supply 12, a pulsed DC magnetic field develops through the core member 5 and has a frequency set in the oscillator 14 by means of the setting knob 11 and an intensity set at the resistor 16 which is adjustable. The stylus member 7 then serves to concentrate the generated magnetic field and to allow the flux to penetrate into a body tissue 17 with which it is positioned in contact.

Figure 2:
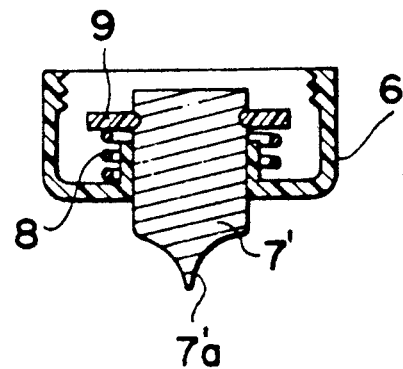
FIG. 2 is a sectional view in elevation diagrammatically illustrating an embodiment of the stylus member having a pointed tip portion.

The leaf spring 9 is detachably secured to the stylus member 7 so that the latter may be removed from the cup 6 and replaced by another stylus member which as shown at 7' in FIG. 2, can have a different configuration which is selected depending on the particular site of the body surface, 7 of a patient and/or his particular symptoms. The stylus member 7, 7' is secured to the cup 6 with the spring 8 and the cup 6 is threaded with the housing 3 to establish a firm contact between the core member 5 and the stylus member 7. The housing 3 and the cup 6 are, of course, composed of nonmagnetic material such as plastic.

The oscillator 14 is designed through the resistors 14a and 14b to variably set its output frequency and thus the frequency of the pulsed DC magnetic field in the range between 1 and 100 Hz. It has generally been found that an individual should be treated with a continuous or DC magnetic field fluctuating or pulsed at a frequency which ranges around 4 Hz in his sleep or when the patient is being induced to sleep, at a frequency which ranges between 7 and 20 Hz when he is at rest or attending to a purely mental activity and at a frequency which ranges around 60 Hz when he is involved in physical labor. No appreciable increase in the effect by using a fluctuating (e.g. pulsed DC) magnetic fied has been observed when the frequency is less than 1 Hz and in excess of 100 Hz. The intensity of the magnetic field should be adjusted in the range between 300 and 30000 Oersteds by means of the variable resistor 16.

Although not shown, means may be provided to detect a change in the impedance which occurs across the input terminals 14a and 14b with a change in the condition of an affected part 17 of the body with which the stylus member 7 contacts and may include a control circuit which, in response to such an impedance change, acts on the variable resistor 16 to automatically control the intensity of the magnetic field in accordance with the condition of the affected part 17.

The stylus member 7 shown in FIG. 1 is formed with a smooth or larger tip surface 7a of gentle slope adapted to be swept over a zone of the body surface 17 in contact therewith, whereas the stylus member 7' shown in FIG. 2 is formed with a pointed tip 7'a adapted to bear upon a "tsubo" or key point on the body surface as in conventional acupuncture treatment.

For replacing stylus members, the cup 6 and elements 7, 8, 9 may be replaced together or the member 7, 7' alone may be replaced.

Figure 3:
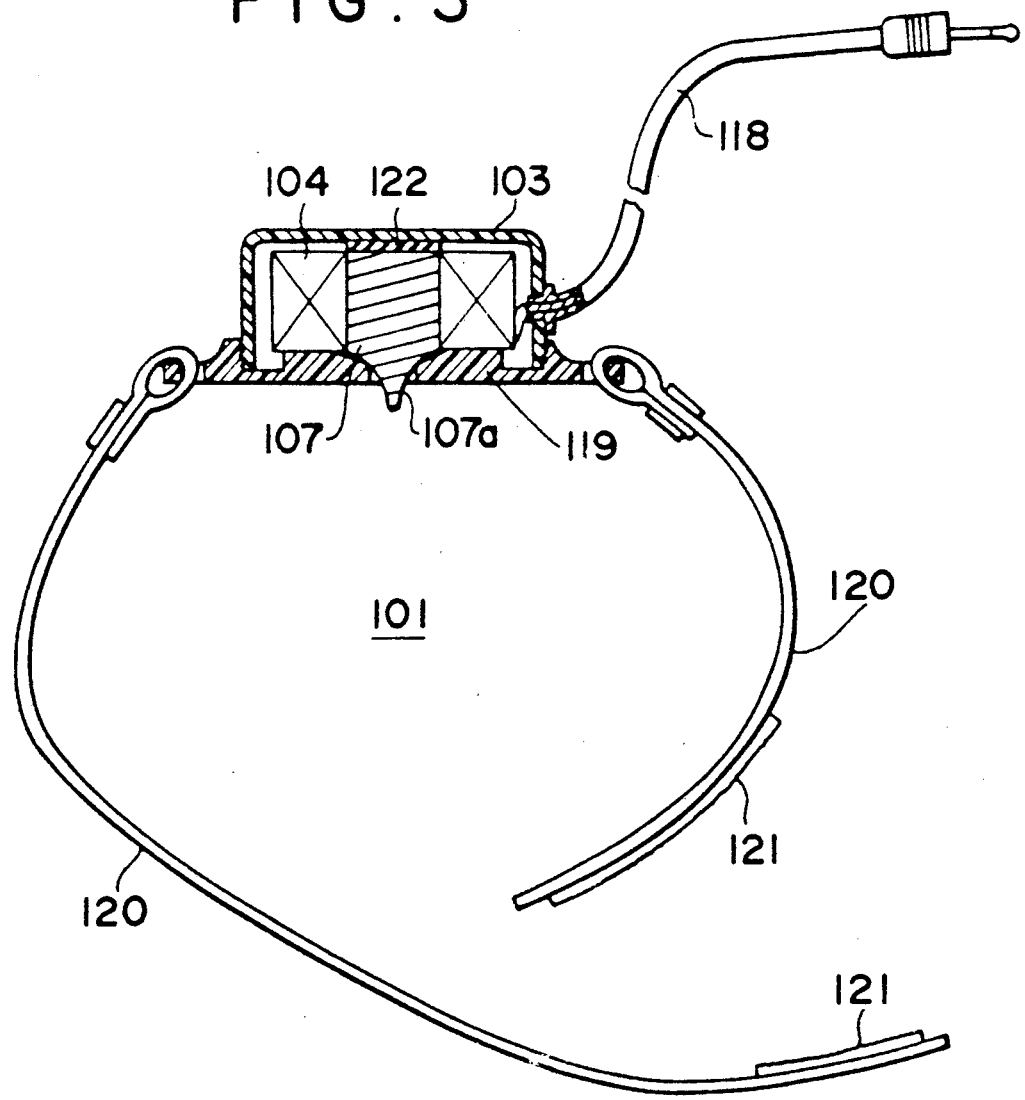
FIG. 3 is a schematic view diagrammatically illustrating a portion of another embodiment of the invention including fastening means.

FIG. 3 shows another device of the invention which may be used as secured in position on an appropriate part of a patient's body. In this embodiment, an electromagnetic coil 104 is shown wound on a magnetically permeable stylus member 107 in a housing 103 and having an input power cord 118 leading out of the housing 103 for connection with an external unit (not shown) of the power supply which may be constructed in a manner as previously or hereinafter described. The housing 103 in the form of a cup is threadedly fitted with a base plate 119 which supports the coil 104 and the stylus member 107 thereon. The tip portion 107a of the latter projects through a central opening 108a formed in the base plate 108, which has a pair of belts 120 hooked thereon. Each of the belts 120 has at its end zone a magic tape 121 applied thereon. The tip portion 107a of the stylus member 107 projected out of the housing 103 is here pointed in a shape similar to that shown in FIG. 2 and thus adapted to precisely rest upon a "tsubo" or key point on the patient body. A cushion material 122 is inserted to fill the space between the top of the stylus member 107 and the housing 103 to reduce the contact pressure or shock with which the pointed tip 107a is pressed against the body tissue.

In the use of the device of FIG. 3, the tip 107a of the stylus member 107 beneath the base plate 119 is positioned to precisely bear upon a given "tsubo" or key point on the patient body (e.g. on the waist) and the belts 120 are worn around an appropriate body part (e.g. around the waist) and fastened thereon with magic tapes 121 to hold the stylus member 107 in the sitting position. Then the power supply circuit is turned on to energize the coil 104 with a fluctuating current, e.g. a pulsed DC, of a predetermined frequency and a predetermined peak current or amplitude. A corresponding magnetic field, e.g. pulsed DC magnetic field, of that frequency and of an intensity corresponding to that peak current or amplitude develops through the stylus member 107 and the resulting magnetic flux leaving the tip 107a penetrates into the "tsubo" or key point. After a desired period of the magnetic treatment, the power supply is turned off to deenergize the coil 104.

Figure 4:
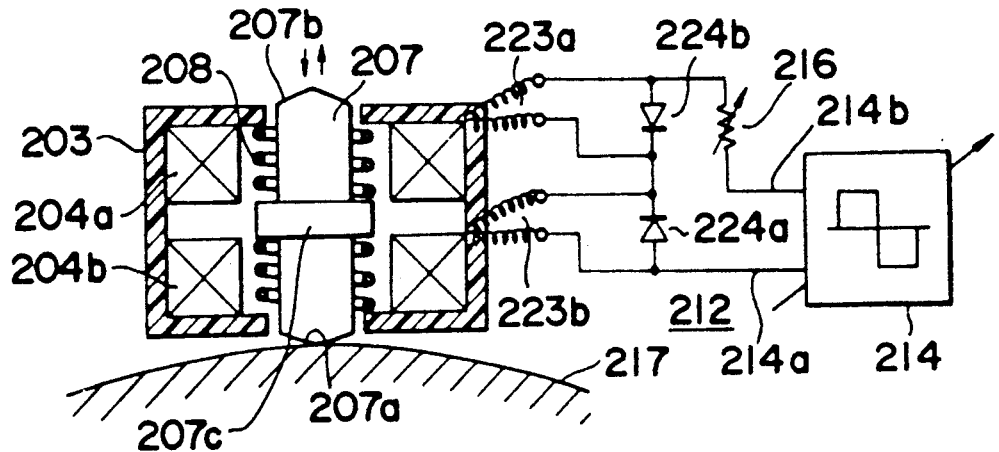
FIG. 4 is a schematic illustration of a further embodiment of the invention wherein the stylus member for applying the magnetic field is electromagnetically vibrated to augment the impetus effect.
Figures 5A, 5B, 5C, 5D:
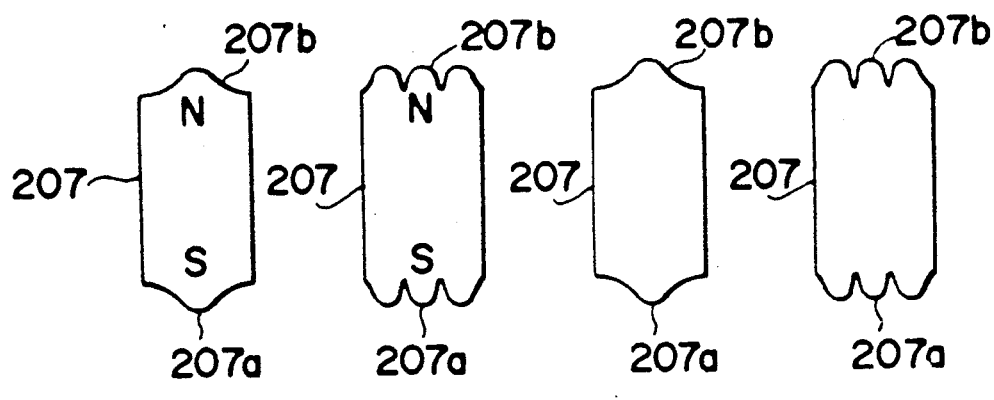
FIGS. 5A, 5B, 5C, and 5D are diagrammatic longitudinal views of various embodiments of the stylus member.

A device of the invention shown in FIG. 4 includes a stylus member 207 having a pair of ends 207a and 207b both of which slightly project from a housing 203 and the first of which is shown in contact with a body surface 217. The stylus member 207 has its central flange 207c supported by a helical spring 208 inserted between the upper and lower walls of the housing 203. The stylus member 207 is thus resiliently supported by the housing 203. Within the latter, a pair of coils 204a and 204b are seated in tandem to surround the stylus member 207 above and below its central flange 207e, respectively.

A power supply 212 for energizing the coils 204a and 204b comprises an oscillator unit 214 designed to provide across its output terminals 214a and 214b a periodic signal of alternating polarity. This periodic signal may, as shown, comprise a succession of alternating rectangular pulses or a positive rectangular half cycle and a negative rectangular half cycle which alternately occur. These positive and negative half cycles which develop at the output terminals 214a and 214b are applied to the coils 204a and 204b, respectively, via conductors 223a and conductors 223b. To enable this, a diode 224a and a diode 224b are connected across the conductors 223b, and the conductors 223a, respectively, so as to conduct the positive half cycles and the negative half cycles, respectively, and to block the negative half cycles and the positive half cycles, respectively. A magnetic field of alternately occurring polarities is thus created by the coils 204a and 204b and applied, concentratedly to the "tsubo" or key point through the stylus member 207 and its lower end 207a in contact therewith or in proximity thereof. An adjustably variable resistor 216 is provided in the power circuit 212 as shown to give a desired intensity of the magnetic field in the range of 300 to 10000 Gauss (surface flux density). The oscillator 214 is capable of frequency adjustment so that, as mentioned before, the fluctuating magnetic field may be of a desired frequency in the range between 1 and 100 Hz.

In operation, the housing 203 is manipulated to bring the tip 207a of the stylus member 207 in engagement with a desired point on the body surface 217. The oscillator 214 is actuated to energize the coils 204a and 204b. Then, positive half cycles or pulses of the output of the oscillator 214 are passed through the diode 224a, the conductors 223a and the coil 204a and negative half cycles or pulses thereof are passed through the diode 224b, the conductors 223b and the coil 204b. The coilsl 204a and 204b are thus alternately energized to produce the periodically reversing magnetic field and to apply, through the stylus member 207 which serves as a field concentrator the periodically reversing magnetic flux to the desired point on the body surface. The stylus member 207 is magnetically permeable and may temporarily be magnetized upon each establishment of a magnetic field. Then, the magnetization of the stylus member 207 may be capable of interacting with the external magnetic field produced by the coil 204a, 204b. For example, when the lower coil 204b is energized to establish the magnetic field directed upwards, the stylus member 207 may be forced downwards. Conversely, when the upper coil 204a is energized to establish the magnetic field directed downwards, the stylus member 207 may be forced upwards. Since the magnetic field forces occur alternately, the stylus member 207 may be brought into a vibration of the frequency established at the oscillator 214. In this manner, the stylus tip 207a may repetitively make and break the contact with the desired point on the body surface 217. Depending on the stroke of this vibration, the external manipulation pressure applied by the housing 203 and exerted on the stylus member 207 via the spring 208 may be adjusted to keep the stylus tip 207a being vibrated in contact with the desired point on the body surface 217. At any event, the vibration of the stylus member 207 brings about an intermittent pressurization and produces recurrent stimulus or impetus on the point on the body surface.

The production of such stimuli or impetus may be achieved in a desired fashion by using one of a variety of different stylus members such as those with different tip forms as shown in FIGS. 5A, 5B, 5C and 5D. Stylus members 207 shown in FIGS. 5A and 5B make use of a permanent magnet whereas those shown in FIGS. 5C and 5D make use of a nonpermanent magnet material. Stylus members 207 of FIGS. 5A and 5C have tips 207a and 207b shaped to possess a simple round projection. Stylus members 207 of FIGS. 5B and 5D have tips 207a and 207b shaped to possess three round projections.

The embodiment of FIG. 4 is, therefore, designed to apply to an affected part a fluctuating magnetic field and flux while subjecting that part to a vibratory stimulus or impetus. In this manner, an intensified stimulating current induction is produced in the blood flow to achieve an enhanced effect of functional recovery and treatment.

Figure 6:
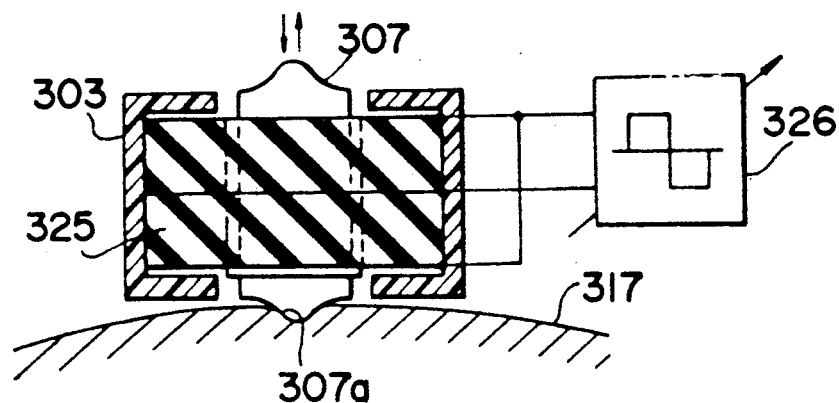
FIG. 6 is a schematic view of a modification of the embodiment of FIG. 3 in which the stylus member is carried on an electromechanical transducer and thereby vibrated.

FIG. 6 shows a modification of the embodiment of FIG. 4 wherein a stylus member 307 formed of a magnetically permeable or permanent-magnetic material carries an electromechanical transducer 325 energized by a power supply 326. When the transducer 325 is energized by the power supply 326, a mechanical vibration is produced therein to vibrate the stylus member 307. When the latter is composed of non-permanent magnet material, coil means is provided and energized by a power supply, both of which are omitted in this FIGURE, to produce a desired fluctuating magnetic field and flux as described before. When the stylus member 307 is composed of a permanent-magnet material, no such coil and power supply is required to produce the magnetic field and flux which is produced directly by the stylus member 307. In FIG. 6, the vibration-stimulating tip portion 307a of the stylus member 307 is shown in engagement with a desired portion of the body surface 317 which is slightly deformed thereby under the engagement pressure.

Figure 7:
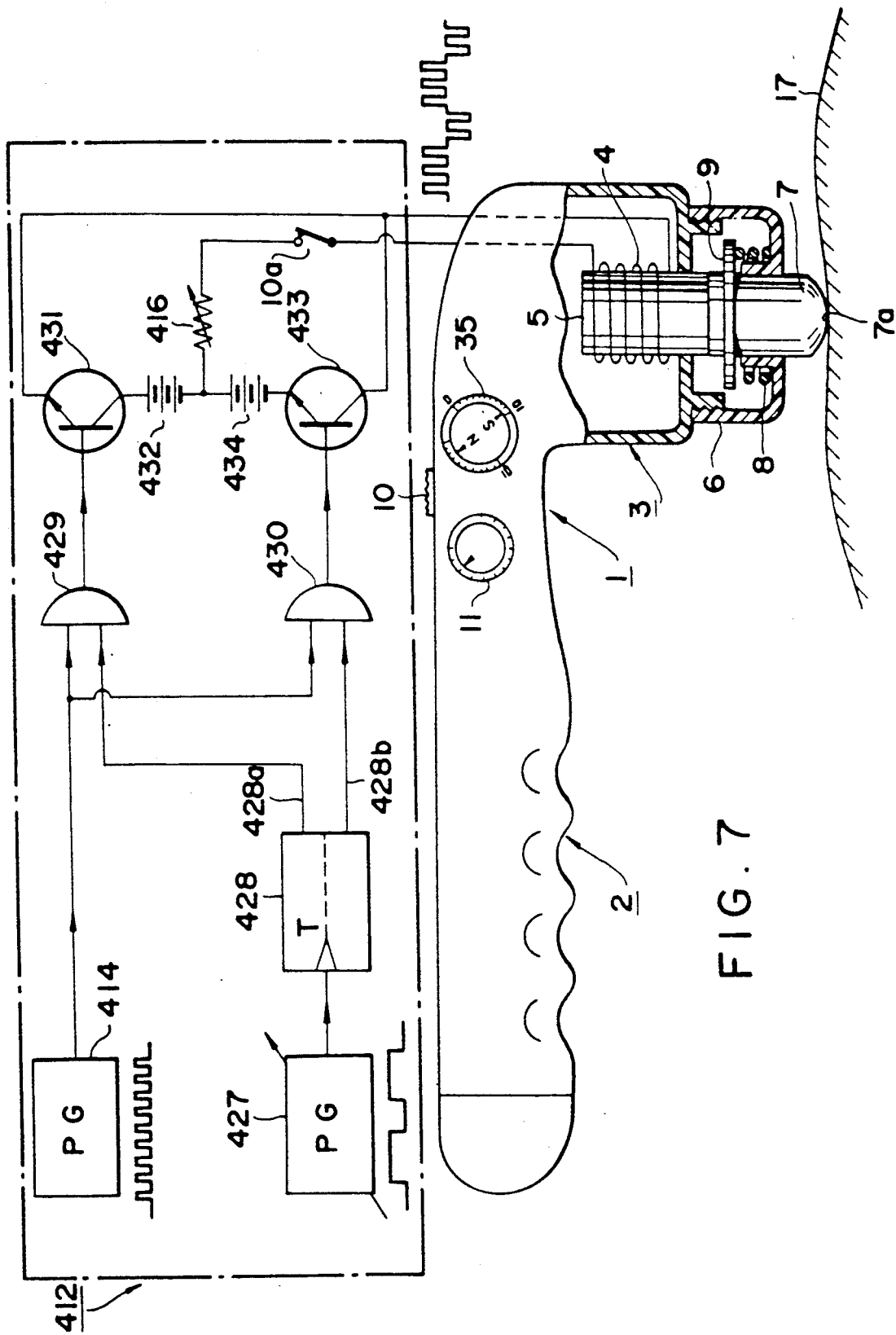
FIG. 7 is a schematic view of a device similar to that in FIG. 1, including a power supply circuit associated with the coil means to furnish a pulsed DC field whose polarity is periodically or aperiodically reversed.

FIG. 7 shows a magnetic treatment device essentially the same as that shown in FIG. 1 and including same parts thereof designated by same reference numerals and a modified power supply circuit, which is designated generally at reference numeral 412, for energizing the coil 4 electromagnetically associated through the core member 5 or directly, with the stylus member 7. The power supply 412 comprises a principal oscillator 414 and an additional oscillator 427. The output of the latter is shown fed to a T-type bistable circuit 428 which has a pair of output terminals 428a and 428b. A first AND gate 429 is provided to combine the output of the principal oscillator 414 and the first output 428a of the bistable circuit 428. A second AND gate 430 is provided to combine the output of the principal oscillator 414 and the second output 428b of the bistable circuit 428. The output of the first AND gate 429 is fed to a first switching transistor 431 which is connected in series with the coil 4, a first DC source 432, a variable resistor 416 and a switch 10a. The output of the second AND gate is fed to a second switching transistor 433 which is connected in series with the coil 4, a second DC source 434, the variable resistor 416 and the switch 10a. The latter represents contacts for the thumb switch 10.

Figure 8:
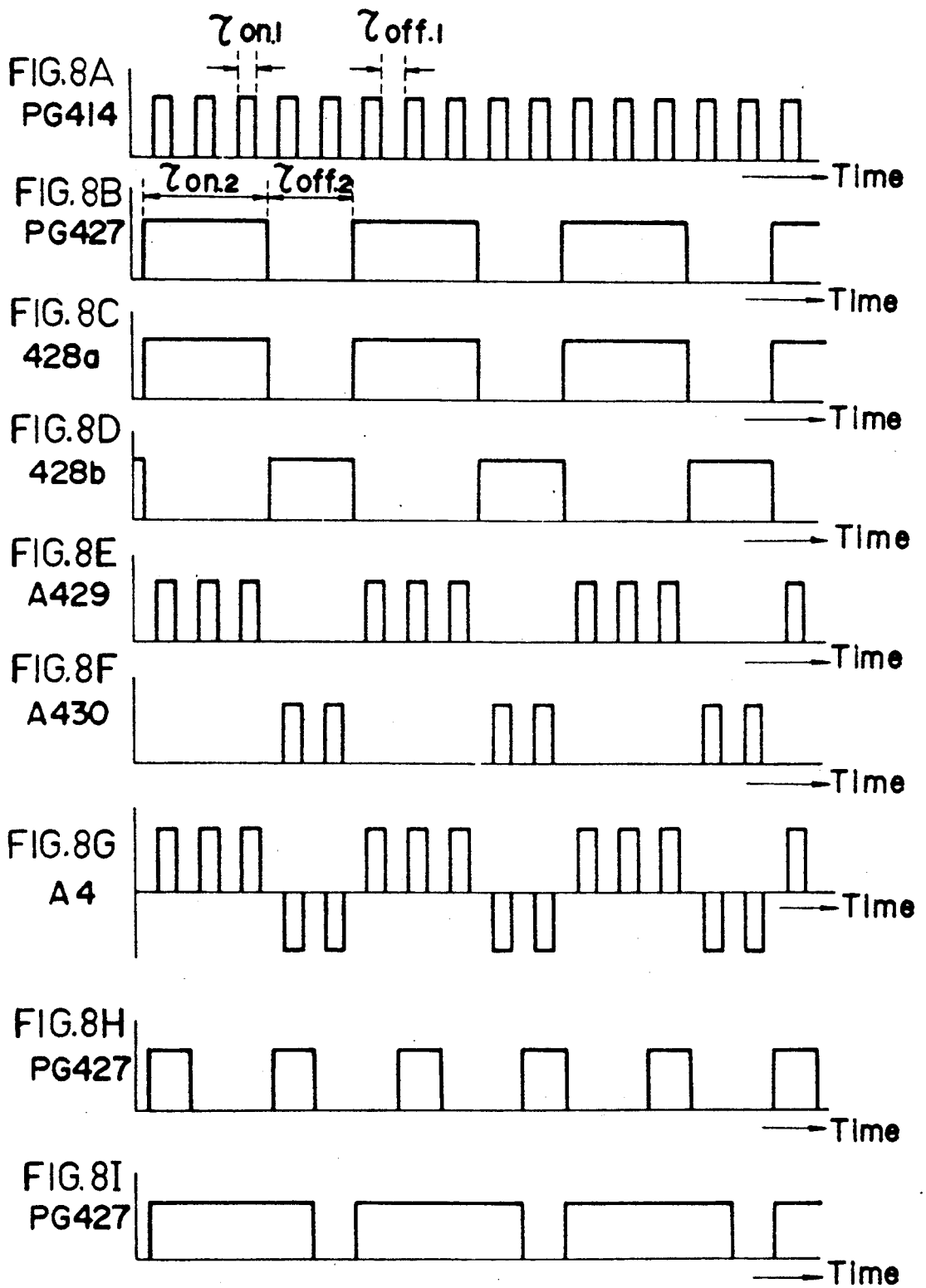
FIGS. 8A through 8I are waveform diagrams illustrating signals which develop at various portions of the circuit in FIG. 7.

The principal oscillator 414 provides a stream of electrical pulses as shown an FIG. 8A, of a frequency ranging between 1 and 100 Hz and having a pulse duration τon.1 and a pulse interval τoff.1. The additional or control oscillator 427 provides a stream of electrical pulses as shown in FIG. 8B, of a different frequency and having a duration τon.2 and interval τoff.2 each of which is longer than τon.1 and τoff.1. The latter pulses are fed to the T-type bistable circuit 428. The first and sescond output terminals 428a and 428b of the latter alternately provide a pulse in the train shown in FIG. 8C and a pulse in the train shown in FIG. 8D. Accordingly, the first AND gate 429 provides an output consisting of time-spaced trains of pulses shown in FIG. 8E whereas the second gate 430 provides an output consisting of time-spaced trains of pulses shown in FIG. 8F. These alternate trains of signal pulses are furnished to the switching transistors 431 and 433, respectively. The transistors 431 and 433 are thus turned on and off accordingly. The first transistors 431 is turned on and off to connect and disconnect the first DC source 432 to the coil 4. The second transistor 433 is turned on and off to connect and disconnect the second DC source 434 to the coil 4. As a consequence, the coil 4 is energized, in a period τon.2, with each train of power pulses of one polarity and, in a period τoff.2, with each train of power pulses of the opposite polarity, as shown in FIG. 8G. Since the DC sources 432 and 434 (and the transistors 431 and 433) are connected to the coil 4 to deliver their output currents flowing in opposite directions through the coil 4, the latter produces a pulsed magnetic field of one polarity and the other polarity which alternately occur in a form shown in FIG. 8G. As a result, the tip 7a of the stylus member 7 is then polarized with time as follows: S-S-S-N-N-S-S-S-N-N- . . . .

The control oscillator 427 should be adjustable as to the duration τon.2 and interval τoff.2 of its output pulses. For example, the control oscillator 427 may be adjusted to provide a stream of its output pulses which have, in relation to the output pulses (τon.1, τoff.1) of the principal oscillator 414, a duration τon.2 and interval τoff.2 as shown ion FIG. 8H or FIG. 8I. It will be seen that in the case of timing of FIG. 8H, the polarities of the tip 7a of the stylus member 7 are switched as follows: S-N-N-S-N-N- . . . . In the case of timing of FIG. 8I, the polirities of the tip 7a of the stylus member 7 are switched as follows: S-S-S-S-N-S-S-S-S-N- . . . . A knob 35 is provided to allow adjustments of such switching sequence of the magnetic field and is associated with time-constant networks in the control oscillator 427 which determine its output pulse duration τon.2 and interval τoff.2.

Figure 9:
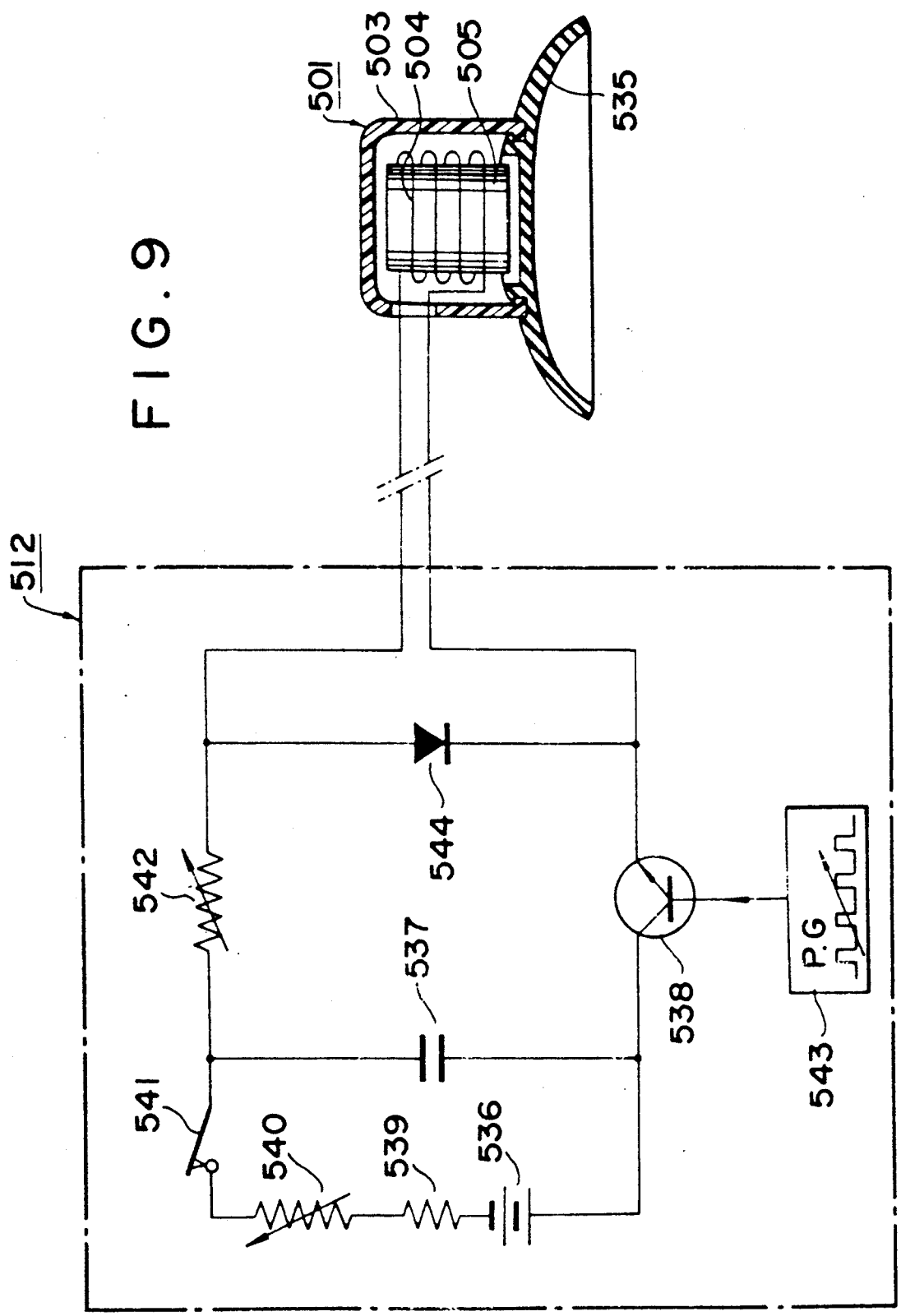
FIG. 9 is a schematic view illustrating a power supply circuit including a capacitor periodically charged and discharged to provide the coil means with a periodic energizing current.

FIG. 9 shows another embodiment of the invention which is modified with respect to both the device structure and the power supply for the coil from those shown earlier. The device 501 of FIG. 9 comprises a core member 505 having the coil 504 wound thereon and received in a housing 503. In this embodiment, a stylus member is omitted. The housing 503 is securely supported on a flexible, vacuum attachment element 535 in the form of a cup and composed of an elastomeric material. The coil 504 is energized by a power supply 512 which basically comprises a DC source 536, a capacitor 537 and a power switch 538. The capacitor 537 on one hand is connected in series with the DC source 536, a fixed resistor 539, a variable resistor 540 and a switch 541 and on the other hand is connected in series with the power switch 538, the coil 4 and a variable resistor 542. The power switch 538 in the form of a transistor is energized by a signal oscillator 543 and a diode 544 is connected to shunt the coil 504.

Upon closure of the switch 541, the DC current of the supply 536 flows to charge the capacitor 537 via the resistors 539 and 540 to a predetermined charging level. The switch 538 is then turned on to allow the charge on the capacitor 437 to be discharged through the coil 504. The oscillator 542 is used to control the timing of turn-on of the switch 538. The switch 541 may be controlled by the oscillator 543 as well to precisely control the alternate charging and discharging of the capacitor 537. When the coil 504 is energized with the discharge current, a magnetic field is instantaneously produced through the coil 504. The diode 544 is used to protect the transistor 538 against the opposed polarity component of the discharge current. As the capacitor 537 charges and discharges repetitively, the magnetic field is repetitively produced through the coil 504 and applied to a portion of the body surface beneath the core member 505 positioned by the sticking element 535.

It has been found that the pulsed magnetic field should have a duration of 0.1 to 10 milliseconds to yield a better treatment result. The variable resistor 542 is provided to allow adjustments of the intensity of the magnetic field in the range between 1000 and 5000 Gauss. The core member 505 is composed of pure iron, ferrite, iron-chromium-cobalt alloy, perm-alloy or sendust. The core member may be dimensioned to possess a diameter of 10 mm for practical purposes.

The use of the attachment element 535 supporting the dedice assembly 501 is advantageous. A petroleum jelly or cream may be applied on the inner wall of the element 535 or on a skin on which the element 535 is mounted. The element 535 may then be pressed around the skin to be secured thereon. Such an attachment element 535 may be applicable to substantially any portion on the body surface.

The device of the invention can be used by and for a patient for a period of 5 to 30 minutes each time and one to five times a day. It has been found that such use of the device of the invention yields a greater result than using a permanent magnet or a magnetic field with a fixed intensity continuously all day in accordance with the prior art.

Figure 10:
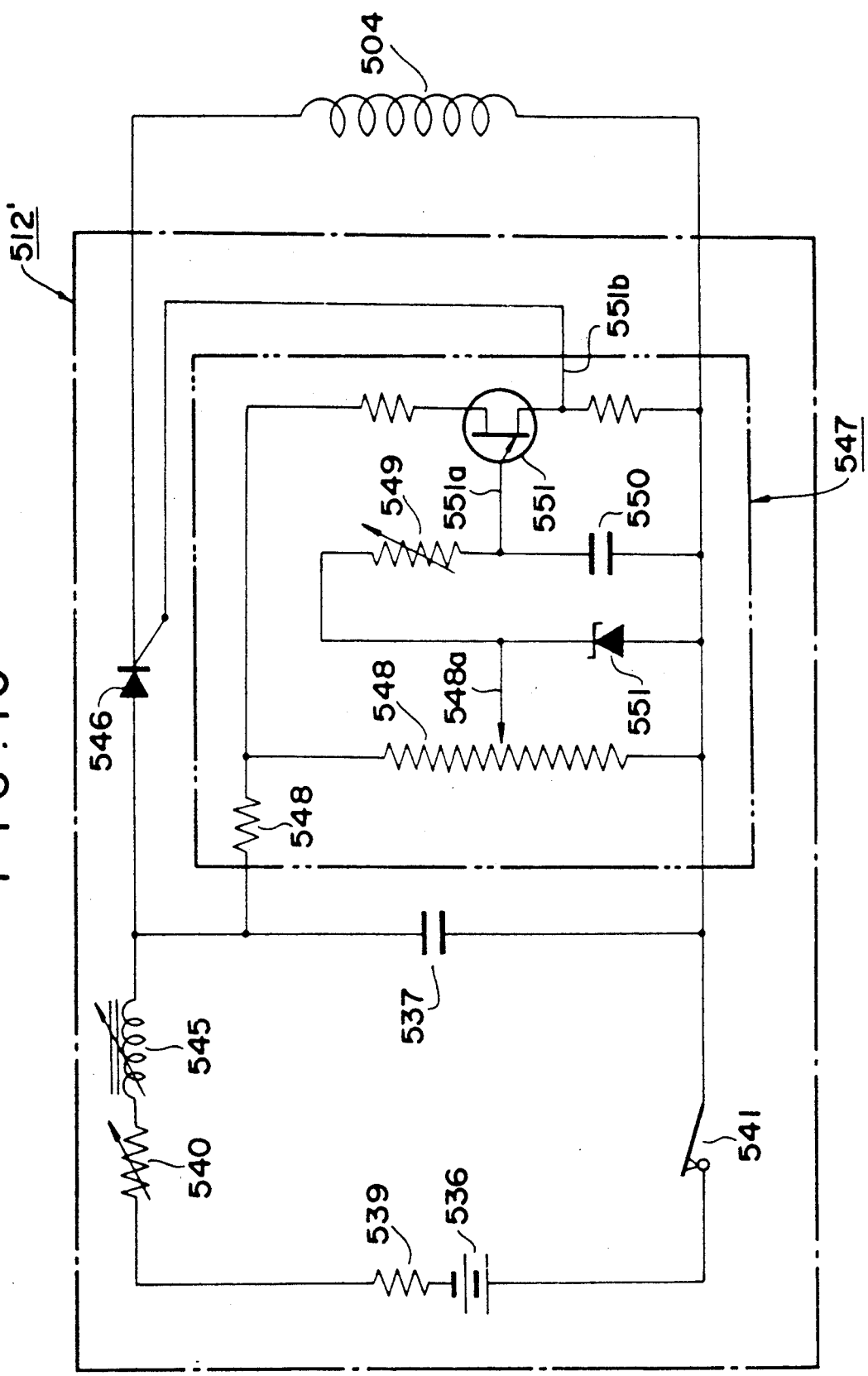
FIG. 10 is a circuit diagram of a modified capacitor-type power supply for energizing the coil means.

FIG. 10 shows a modification of the capacitor-type power supply for the coil 504 shown in FIG. 9. The modified supply 512' comprises a charging circuit for the capacitor 537 including DC source 536, the fixed charging resistor 539, the variable resistor 540, the switch 541 and a charging inductor 545 which is shown adjustable. The discharging circuit for the capacitor 537 comprises a thyristor 546 which is controlledly turned on by a control switching circuit generally designated at 547. The control switching circuit 547 comprises a resistor 548 connected across the capacitor 537 to sense its charging voltage. A series circuit of a variable resistor 549 and a capacitor 550 is connected across an adjustable tap 548a of the sensing resistor 548 in parallel with a Zener diode 551 to constitute a time-constant network for defining the on-off frequency of the thyristor 546. A unijunction transistor 551 connected across a portion of the sensing resistor 548 is controlled by a terminal voltage of the capacitor 550 being applied to its gate electrode 551a and has its drain electrode 551b connected to a control electrode of the thyristor 546.

When the voltage builds up in the capacitor 537 to the level determined by the position of the tap 548a and the rating of the Zener diode 551, the unijunction transistor 551 sustains a current flow through its drain electrode 551b, thereby rendering the thyrister 546 conductive. This allows the charge on the capacitor 537 to be discharged through the coil 504. The unijunction transistor 551 is cut off after a conductive period determined by the time constant of the network 549, 550.

Figure 11:
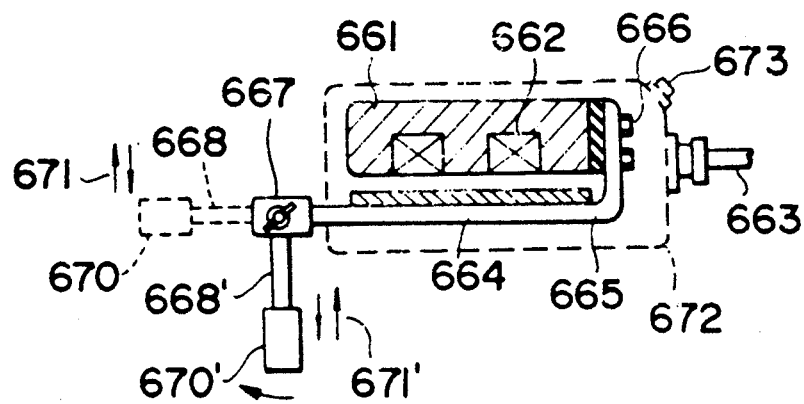
FIG. 11 is a schematic view diagrammatically illustrating a conventional massaging apparatus incorporating a device according to the invention.

In a further embodiment of the invention shown in FIG. 11, a fixed core member 661 constituted by laminated E-shaped silicon steel plates has a coil 662 wound thereon. The coil 662 is energized by a commercial AC fed through leads 663 to produce magnetic fluxes through the fixed core member 661. A movable iron plate 664 is carried by an L-shaped member 665 whose one end is attached to one end of the fixed core member 661 by means of screws 666 so that the plate 664 is spacedly juxtaposed with the core member 661 and with the coil 662 energized, the member 665 is vibrated. The member 665 terminates with a chuck 667 on which a shank 668, 668' carrying a device of the invention 670, 670' is detachably mounted.

Figure 12:
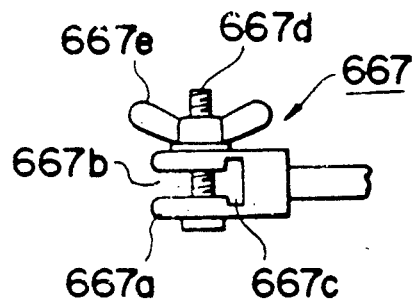
FIG. 12 is a schematic view in section illustrating a portion of the apparatus of FIG. 11.
Figure 13A:
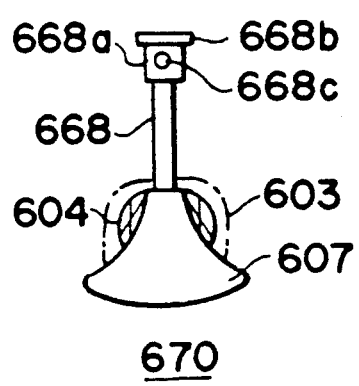
FIGS. 13A and 13B are longitudinal schematic views diagrammatically illustrating different stylus assemblies which may be used in the apparatus of FIG. 11.
Figure 13B:
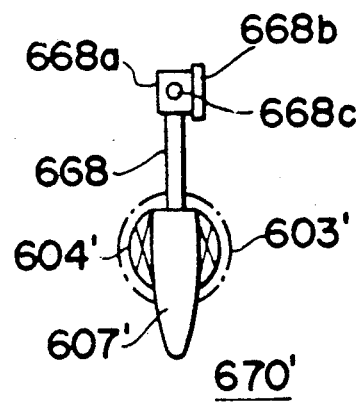

As shown in FIGS. 12 and 13A and 13B, the chuck 667 comprises a U-shaped clamping element 667a having a space 667b into which the mounting end 668a of the shank 668 is inserted. This end includes a key element 668b adapted to mate with a positioning depression 667c in the space 667b. A bolt 667c is inserted through openings (not shown) in the clamping element 667a and through an opening 668c formed in the mounting end 668a of the shank 668 and a butterfly nut 667e is then threaded with the bolt 667d to firmly secure the shank 668 supporting the device 670 to the vibratile member 665.

The device 670, 670' as shown in FIGS. 13A and 13B comprises a stylus member 607, 607' having a coil 604, 604' wound thereon, the coil being energized by an electric current of fluctuating intensity (e.g. AC) to produce a fluctuating (e.g. AC) magnetic field and flux which is applied through the stylus member 607, 607' to a selected surface zone of the patient's body surface as has been described.

The device 670, 670' may have a stylus member 607, 607' which as shown in FIGS. 13A and 13B is formed with a desired shape along its tip area adapted in contact with the body surface. The stylus member 607 shown in FIG. 13A is preferred to exert a rubbing or kneading effect on the body surface whereas the stylus member 607' shown in FIG. 13B is preferred to exert a tapping or stroking effect on the body surface. The device 670 of FIG. 13A should be secured via the chuck 667 to the vibratile member 665 to extend generally coaxial therewith so as to be vibrated (i.e. swingingly vibrated) as indicated by arrows 671. The device 670' of FIG. 13B should be secured via the chuck 667 to the vibratile member 665 to extend generally perpendicular thereto so as to be vibrated (i.e. reciprocatingly vibrated) as indicated by arrows 671'.

The vibrating unit, 661, 662, 664, 665 is shown accommodated in a casing 672 provided with a manual switch 673 for switching on and off the energization of the coil 662 (in the vibrator) and of the coil 604 (for magnetic treatment). The stylus member 607, 607' having the coil 604, 604' wound thereon may be contained in a housing 603, 603' so that its end portion is projected therefrom for engagement with a preselected surface zone of the body surface of a patient as has been described.

In the description of FIG. 3, the expression "magic tape" is intended to imply a tape which becomes adherent to an adjacent such tape simply by bringing the two tapes into contact or close proximity with one another. Such tapes may utilize magnetic attraction effects, or the self-attachment properties of tapes comprising respectively arrays or hooks and arrays of loops (such as tapes available commercially under the trade name VELCRO), for example.

There is thus provided an improved device as well as method for magnetic medical treatment.

What is claimed is:

1. A magnetic treatment device comprising:
   coil means;
   power supply means for energizing said coil means with a periodic current of a predetermined frequency to produce through said coil means a corresponding time-varying, periodic magnetic field of said predetermined frequency;
   positioning means operable to position said magnetic field selectively at a preselected surface zone of the body surface of an individual;
   field concentrator means constituted by a stylus member electromagnetically associated with said coil means and positionable with said positioning means for engagement with said preselected surface zone of the body surface of the individual for selectively applying said magnetic field to said preselected surface zone;
   housing means for accommodating said coil means therein and carrying said stylus member to hold it at least in part projected therefrom for engagement with said preselected surface zone; and
   spring means associated with said housing means for supporting said stylus member resiliently therewith to reduce a contact shock of said stylus member against said body surface of the individual.

2. The device defined in claim 1, further comprising a handle mechanically coupled with said housing means and constituting at least in part said positioning means for positioning said stylus member in a predetermined engagement relationship with said preselected surface zone of the body surface of the individual.

* * * * *